United States Patent [19]

Blessing et al.

[11] Patent Number: 4,672,851
[45] Date of Patent: Jun. 16, 1987

[54] ACOUSTIC EVALUATION OF THERMAL INSULATION

[75] Inventors: Gerald V. Blessing, Frederick; Daniel R. Flynn, Gaithersburg, both of Md.

[73] Assignee: The United States of America as represented by the Secretary of Commerce, Washington, D.C.

[21] Appl. No.: 868,483

[22] Filed: May 30, 1986

[51] Int. Cl.[4] .............................................. G01N 29/00
[52] U.S. Cl. ......................................... 73/597; 73/599
[58] Field of Search ................. 73/574, 589, 599, 579, 73/597

[56] References Cited

U.S. PATENT DOCUMENTS

| | | | |
|---|---|---|---|
| 3,345,863 | 10/1967 | Henry et al. | 73/597 |
| 3,654,072 | 4/1972 | Massa | 73/599 |
| 3,737,844 | 6/1973 | Yokoyama et al. | 73/599 |
| 4,117,732 | 10/1978 | Brazhnikov | 73/599 |
| 4,481,820 | 11/1984 | Thomann | 73/599 |
| 4,581,935 | 4/1986 | Breazeale | 73/599 |

Primary Examiner—Anthony V. Ciarlante
Attorney, Agent, or Firm—Eugene J. Pawlikowski; Alvin J. Englert; Robert V. Sloan

[57] ABSTRACT

An acoustic method for measuring the quantity and installed density of thermal insulation includes introducing a sensing apparatus comprised of one or two acoustic transducers which are so placed as to measure the attenuation and/or phase shift of acoustic waves passing through the insulation. The thermal conductivity for a given insulation material may be monitored as a function of insulation depth by relating the acoustic amplitude and/or phase to a predetermined relationship for that particular insulation material. The relationship may be simply a set of tabular guides relating the quantity of insulation to an amplitude or phase value. This method may be applied to material in an enclosed space, an attic for example where remote access would be desirable, or to material in an open space. In the case of an attic enclosure, the apparatus introduced through a small ceiling hole may be subsequently unfolded or manipulated to place the transducers and possibly a reflecting target in the desired location relative to each other for carrying out the desired measurements.

8 Claims, 9 Drawing Figures

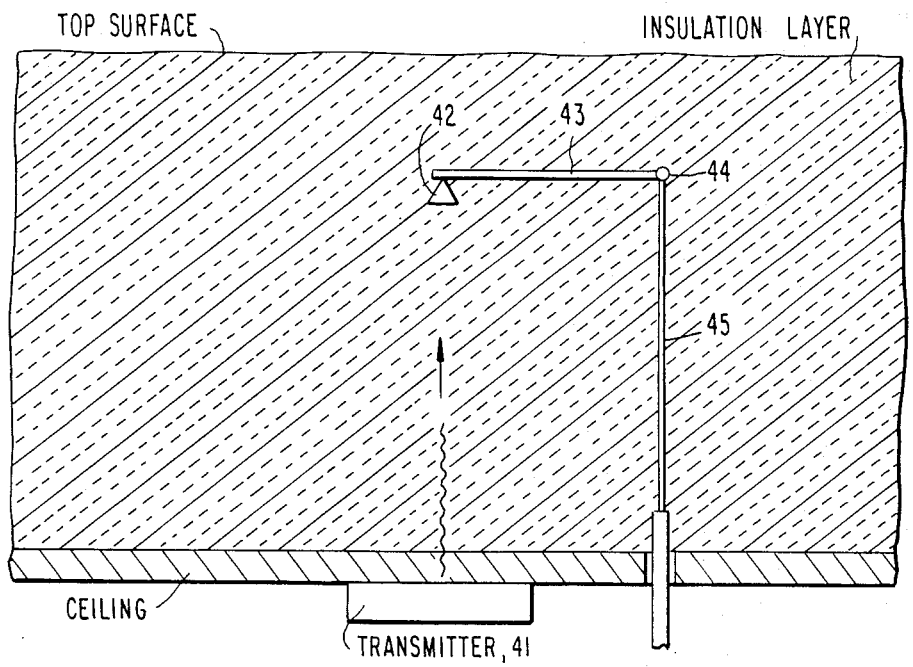
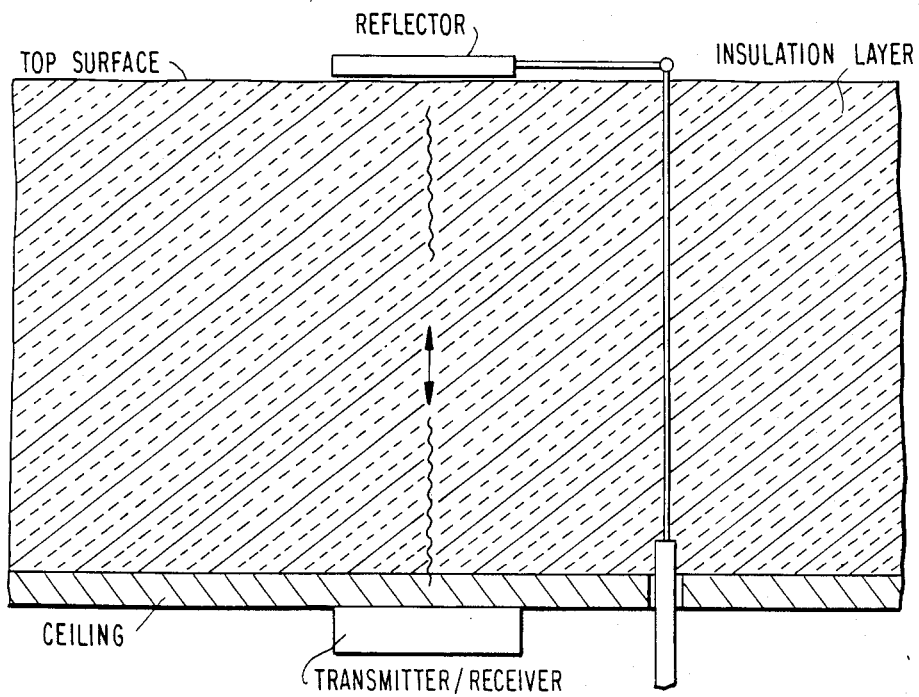

ACOUSTIC EVALUATION OF THERMAL INSULATION

BACKGROUND OF THE INVENTION

The present invention is directed to an acoustic method and apparatus for measuring the quantity and installed density of thermal insulation and more specifically to the arrangement of one or more acoustic transducers and/or reflecting means in or adjacent the insulation for directing acoustic waves through the insulation to measure the attenuation and/or phase shift of the acoustic waves passing through the insulation.

When a sound wave passes through a porous material, such as a loose-fill insulation, the sound wave undergoes both amplitude attenuation and a phase shift that depend on the nature of the material and the frequency of the sound. For example the sound attenuation of fibrous materials is dependent upon the material itself, the distribution of fiber diameters, the surface condition of the fiber, the binder, the bulk density, and the type and density of the gas filling the pores of the material. These same factors also affect the thermal conductivity of fibrous material.

These factors are related in the following way. The sound pressure, p, associated with a plane acoustic wave traveling in the positive x-direction in a porous medium can be expressed as $$p(x,t) = p(0,t) \exp(-\gamma x),$$

where t is time and the complex propagation coefficient $\gamma$ can be written as $$\gamma = \alpha + j\beta,$$

where the real part is called the attenuation coefficient and the imaginary part $\beta$ is the phase coefficient. The attenuation coefficient, which is a property of the porous medium and of the frequency of the sound wave, determines the decay of the sound intensity with distance in the medium. The phase coefficient, which also is a property of the medium and the sound frequency, determines the speed of sound propagation through the medium.

If the dependence of the attenuation coefficient on the bulk density or the porosity of the medium is known, a measurement of the sound attenuation over a given distance enables calculation of the density. Similarly, if the dependence of the phase coefficient or the sound speed on the density is known, a measurement of the speed of sound enables calculation of the density of the medium.

For randomly oriented fibrous material, the attenuation coefficient is known empirically to depend upon the bulk density, $\rho$, of the insulation, the average fiber diameter, d, and the sound frequency, f, according to the approximate relationship $$\alpha = \alpha_0 \cdot \left(\frac{\rho}{\rho_0}\right)^{0.9} \cdot \left(\frac{d_0}{d}\right)^{1.2} \cdot \left(\frac{f}{f_0}\right)^{0.4},$$

where $\alpha_0$ is a reference attenuation coefficient corresponding to the values $\rho = \rho_0$, $d = d_0$, and $f = f_0$. The exponents 0.9, 1.2, and 0.4 vary somewhat and should be determined empirically for a given material. For a given type of fibrous insulation, the average fiber diameter is fixed. Since the sound frequency can also be fixed experimentally, this equation reduces to a simple relationship between the attenuation coefficient and the bulk density of the insulation. Similar types of relationships can be developed for types of thermal insulation other than fibrous materials.

For randomly oriented fibrous material, the phase coefficient is known empirically to be given approximately by $$\beta = \frac{2\pi f}{c} + \left(\beta_0 - \frac{2\pi f}{c}\right) \cdot \left(\frac{\rho}{\rho_0}\right)^{1.1} \cdot \left(\frac{f_0}{f}\right)^{0.7} \cdot \left(\frac{d_0}{d}\right)^{1.4},$$

where $\beta_0$ is a reference phase coefficient and c is the acoustic wave speed in air. The exponents should be confirmed experimentally. For a given material (i.e., a given fiber diameter) and sound frequency, this equation provides a simple relationship between the phase coefficient and the bulk density of the insulation.

It is well known that the effective thermal conductivity of a given loose-fill insulating material depends upon the bulk density of that material. For mineral fiber insulations, the effective thermal conductivity, of relatively thick insulation is related to the bulk density, $\rho$, of the material by an equation of the form $$\lambda = A + B\rho + \frac{C}{\rho},$$

where A, B, and C are constants, A representing the thermal conductivity of the gas (air) filling the insulation, $B\rho$ representing heat conduction through the fibers and the interaction of that conduction with the surrounding gas, and $C/\rho$ representing the radiative heat transfer through the porous insulation. If this relationship is known for a given type of insulation, and the bulk density is determined from experimental measurements of the attenuation coefficient and/or the phase coefficient the thermal conductivity can be computed.

A method and apparatus for measuring characteristic features of fibrous materials is disclosed in U.S. Pat. No. 4,481,820, to Thomann, granted Nov. 15, 1984. The method disclosed in this patent relates to the measurement of fibrous materials such as slivers and rovings by ultrasonics. In a suitable arrangement of a sound source and a sound pickup with the fibrous material disposed therebetween, only those sound waves arrive at the sound pickup which have penetrated the fibrous material. All lagging disturbing signals which are generated by reflections and interferences are suppressed by a pulsed operation of the sound source and by the corresponding gating of the sound pickup, as a result of which, a value to be measured, namely, the quantity of fibers present at any time in the measuring data, is substantially free from disturbing influences. In order to accomplish this, the fibrous material, in particular a sliver or the like, is guided by lateral boundary surfaces such that all the sound waves are forced to penetrate the fibrous volume in order to arrive at the pickup from the source. The lateral boundary surfaces are preferably formed by parallel plates, the magnitude of compression being selected such that the fibrous material rests closely against the plate. Therefore such a method and apparatus would not be suitable for the measurement of the quantity and density of installed thermal insulation.

Post installation measurement of insulation layers is necessary to ascertain that the correct amount of insulation has in fact been installed. The widely used cookie cutter method has been found unsatisfactory by regulatory agencies for several reasons. This method entails measuring the thickness and cutting out samples of the insulation from representative locations in an attic or other insulated region, placing them in bags, taking them outside of the attic, weighing them and finally restoring the specimens to the places, whence they were originally removed. The weight, thickness and dimension of the removed specimens yield the volume and density of the insulation which can be used to estimate the insulating value or thermal resistance from a previously established relationship for a given insulating material. However many problems are associated with this method, such as difficulties encountered in entering the attic space through a small scuttle hole, walking over ill-defined attic wood frames which are often hidden beneath several inches of thick loose-fill insulation, and removing reproducible and well defined specimens and restoring them to the spots from which they were removed. It has been estimated that the error associated with this method is fifteen to twenty percent.

SUMMARY OF THE INVENTION

The present invention provides a new and improved apparatus for evaluating thermal insulation by an acoustic technique capable of measuring the thickness and a quantity proportional to the density of a thermal insulation layer by remote means not requiring bodily access into an attic. Thus, since all of the measurements can be made in situ, all of the problems attendant the prior method discussed above are overcome.

The present invention provides a new and improved method and apparatus for determining the thickness, density, thermal conductivity of insulation by acoustic means wherein the attenuation and/or phase (sound speed) of acoustic waves passing through the insulation are measured and correlated with predetermined relationships for given insulation materials. From these measurements, the heat flow resistance value, referred to as "R value" in the industry, may be readily determined. The optimum operational wave frequency may be sonic or ultrasonic depending upon the type of insulation, the thickness of the insulation and the desired resolution. The wave excitation technique may be continuous-wave, pulse, swept frequency, or a multiple of frequencies, once again depending upon the insulation parameters and on the particular application approach taken. Obtaining data at more than one frequency by a swept frequency or at multiple discrete frequencies would enhance material characterization and increase the reliability of a correlation between acoustic and insulating properties.

The present invention provides a new and improved method and apparatus for evaluating thermal insulation by acoustic techniques wherein a single probe system having an acoustic transducer operating in the pulse-echo mode would be introduced into the attic space with the acoustic signal being directed vertically through the insulation for reflection off the ceiling or off a separate reflector introduced with the probe, or wherein a dual probe system is introduced into the attic with sending and receiving transducers disposed in a horizontally spaced apart relation whereby the acoustic signals will be translated from one transducer to the other through the insulation material. In the event it is impossible to obtain physical access to the attic space the probe or probes may be inserted into the attic through very small holes drilled through the ceiling at the desired locations which could easily be repaired upon completion of measurements.

The foregoing and other objects, features and advantages of the invention will be apparent from the following more particular description of a preferred embodiment of the invention as illustrated in the accompanying drawings.

BRIEF DESCRIPTION OF THE DRAWINGS

FIG. 8 shows a fifth embodiment of the present invention wherein the transmitting transducer is mounted adjacent to the ceiling underside and the receiving transducer is mounted on the end of a probe in or adjacent the insulation layer.

FIG. 9 shows a sixth embodiment of the present invention wherein the transmitting and receiving transducers are mounted adjacent to the ceiling underside, while a reflector is inserted through a ceiling hole and mounted on the end of a probe on top of the insulation layer.

DETAILED DESCRIPTION OF THE INVENTION

Figure 1:
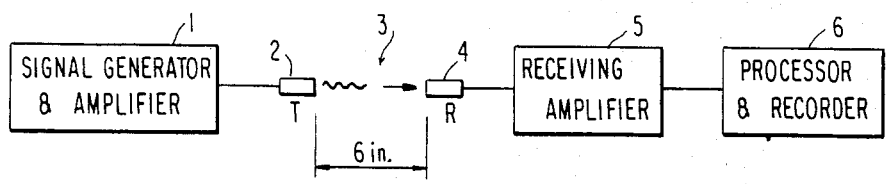
FIG. 1 is a schematic diagram of a two transducer test configuration for demonstrating the sensitivity of acoustic waves to thermal insulation thickness.
Figure 2:
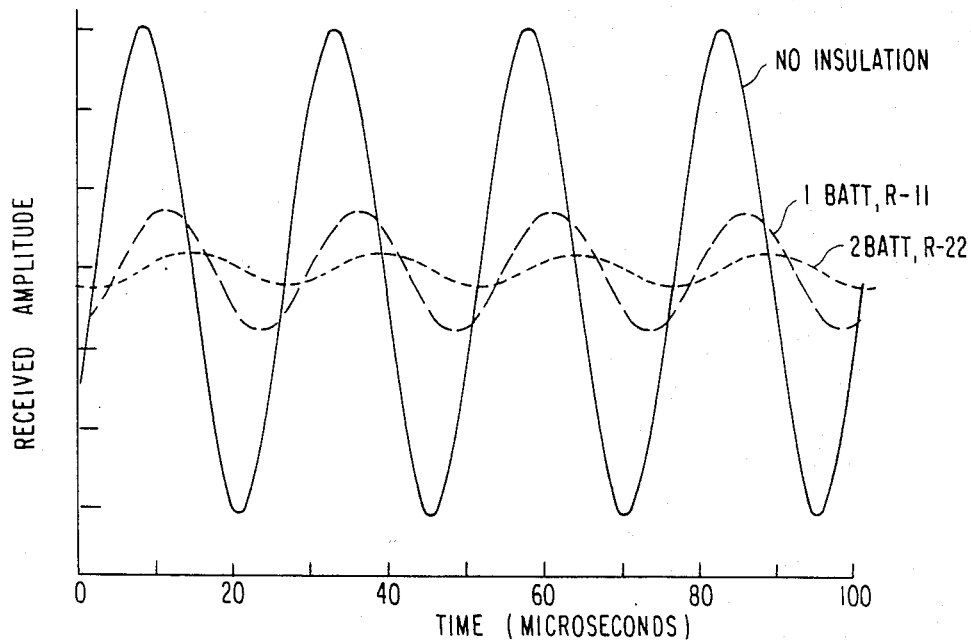
FIG. 2 is a graph showing the received signal wave amplitude in volts plotted as a function of time for three different degrees of insulation.
Figure 3:
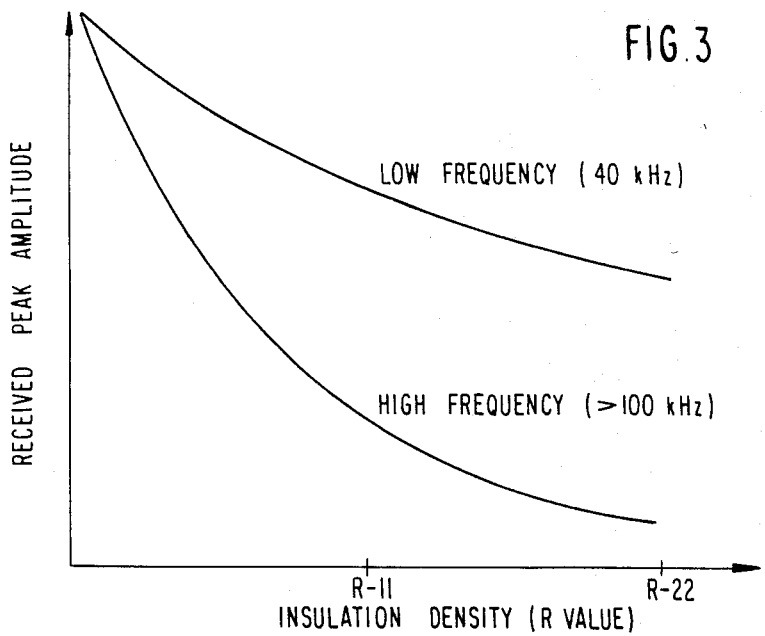
FIG. 3 is a graph showing the peak amplitude of the received signals of FIG. 2 plotted as a function of insulation density, or of R value, at two acoustic frequencies.

A principle of the present invention can be demonstrated with the test configuration of the apparatus as illustrated in FIG. 1. An electro-mechanical transducer 2 which acts as a transmitter and an electro-mechanical transducer 4 which acts as a receiver are situated facing each other at a separation distance of six inches. A signal generator and amplifier 1 provides a signal to the transducer 2 which transmits an acoustic signal across the gap 3 to the receiver transducer 4 which provides an output signal to an amplifier 5 the output of which is connected to a signal processor and recorder 6. Using the same transmitted signal the amplitude and phase of the received signal were measured with (a) no insulation between the transmitter 2 and the receiver 4, (b) one R-11 layer of commercially available batt material intervening, and (c) two R-11 layers intervening. The results for these three situations are shown in FIG. 2 for an operating frequency of 40 kHz. The signal amplitude is observed to decrease with an increasing quantity of insulation due to wave scattering. Plotting the peak amplitude values as a function of insulation R-value in FIG. 3 reveals an exponentially decreasing amplitude for a given frequency which can be expected for the ultrasonic wave attenuation. Furthermore there is a noticeable horizontal time shift of the wave forms in FIG. 2 with an increase in insulation. This phase shift or velocity change may be used to corroborate the amplitude results or in place of the amplitude measurements as an independent measure of the insulation value.

There are several arrangements of sound source (transmitter) and sound receiver that can be used for the in situ acoustic evaluation of thermal insulation. The sound source can be located in the attic and transmit sound down through the insulation to a receiver located in the insulation or at the upper surface of the ceiling; alternatively the sound can reflect back from the ceiling to a receiver located in the attic. The sound source can be located on the ceiling side of the insulation, where it either protrudes through a hole in the ceiling or where the ceiling itself is vibrated and acts as a sound source, and transmits sound up through the insulation to a receiver located in the insulation or in the attic; alternatively the sound can bounce off of a reflector at the upper surface of the insulation and return to a receiver located at the ceiling. (In those applications utilizing a reflector, the same transducer can be used both as a transmitter and as a receiver.) Alternatively, the transmitter and the receiver can be at the same vertical height within the insulation, with the sound being transmitted horizontally. In this arrangement, the transducers can either be inserted into the insulation from the attic space above or through small holes in the ceiling below. Regardless of the particular configuration of transmitter and receiver, a wide variety of transducers can be used for the acoustic measurements of the sound attenuation or the sound speed in thermal insulations.

The sound source (or the sound source and the microphone, if a single transducer is used for both purposes) can be a piezoelectric transducer, a condenser microphone, or an electret microphone. The type of transducer used in intrusion alarms and in automatic door opening systems, or that used in the auto focusing systems in some cameras can be quite satisfactory, as can many types of ultrasonic transducers normally used for industrial inspection or for measurements of level or fluid flow. High frequency sonar transducers of the type normally used underwater can also be used.

If a separate transducer is used as the microphone, it can be relatively small. High frequency piezoelectric microphones are relatively inexpensive, rugged, and ideally suited for the purpose. Electret microphones and condenser microphones are also satisfactory.

When the sound is caused to pass directly through the ceiling material, without a hole, a more powerful sound source is needed since the ceiling must be vibrated sufficiently to radiate sound from its upper surface. In this form of the measurement, an electro-mechanical or piezoelectric shaker can be used. When a large transducer can be used as the source, it can be beneficial to mount the transducer at the focal point of a parabolic reflector so that a large sound beam, of the order of six to twelve inches in diameter, can be used to sample a large area of the insulation under test.

In this special case where the top side of the insulation may be accessible via a scuttle hole, a high frequency electrodynamic tweeter loudspeaker suspended from a pole can be used as the source, beaming the sound down through the insulation to reflect from the upper surface of the ceiling and then return to the attic space where the returning sound can be picked up using the tweeter loudspeaker as a microphone or by using a separate microphone.

Figure 4:
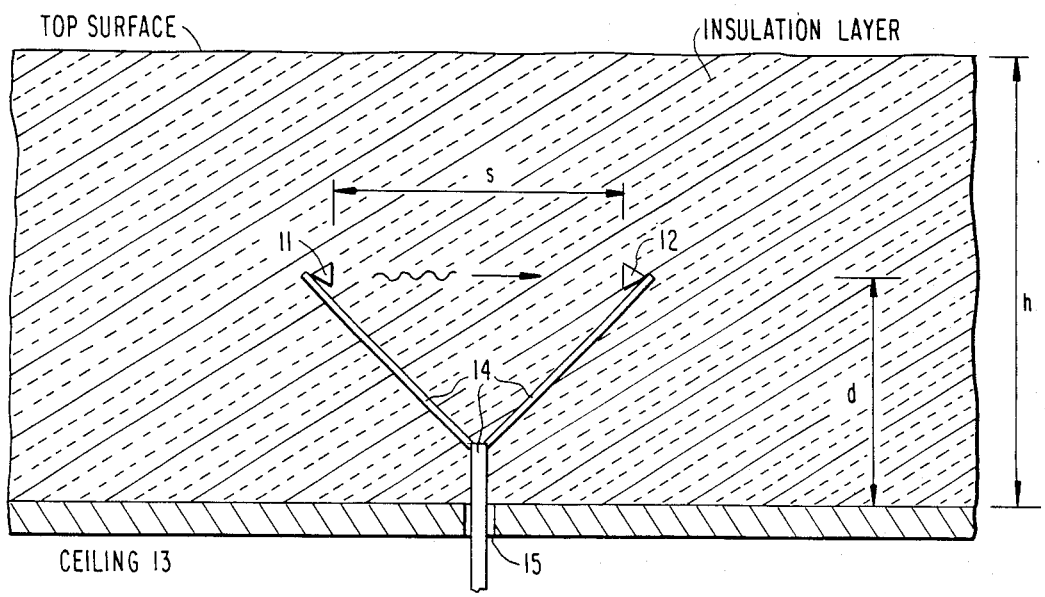
FIG. 4 discloses a first embodiment of the present invention utilizing two horizontally spaced apart acoustical transducers mounted on a single probe.
Figure 5:
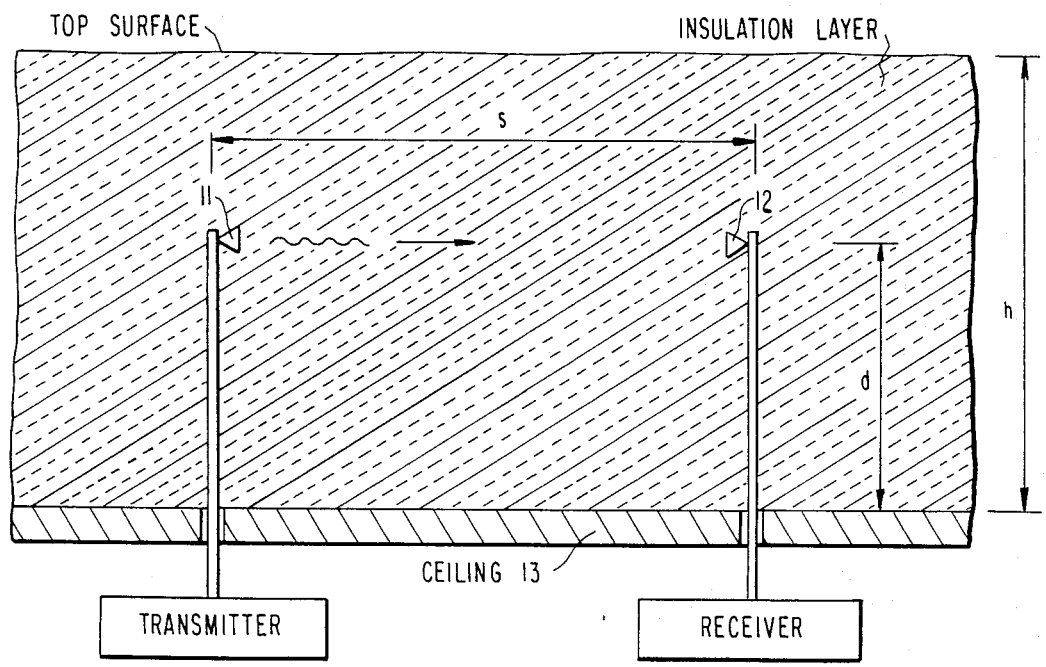
FIG. 5 shows a second embodiment of the present invention utilizing two horizontally spaced apart acoustical transducers on separate probes.

Analogous to the test configuration the apparatus as shown in FIG. 4 is suitable for measuring the insulation value of an installed insulation layer in an enclosed space such as an attic to which access is not available. A small hole 15 may be cut in the ceiling 13 and a probe 14 inserted therethrough into an insulation layer having a depth h. A transmitting transducer 11 and a receiving transducer 12 may be mounted on suitable extensions of the probe 14 which may be retracted or brought together in any suitable manner during insertion through the hole 15 and subsequently be spread apart into the position as illustrated in FIG. 4 with the transducers 11 and 12 spaced from each other in the insulation layer by a distance s. The transducers 11 and 12 may be located at any selected height d within the insulation layer and a density profile of the insulation layer can be achieved by taking a plurality of measurements at different heights d. It is also possible that the two transducers 11 and 12 may be inserted by separate probes through two separate holes spaced apart by a distance s, as shown in FIG. 5. The thickness h of the insulation layer can also be determined by making measurements at different height d until such time as the measurements indicate open air between the transducers. Once this occurs, it is a simple matter to merely mark the distance on the probe and the thickness h can be readily calculated on withdrawal of the probe.

Figure 6:
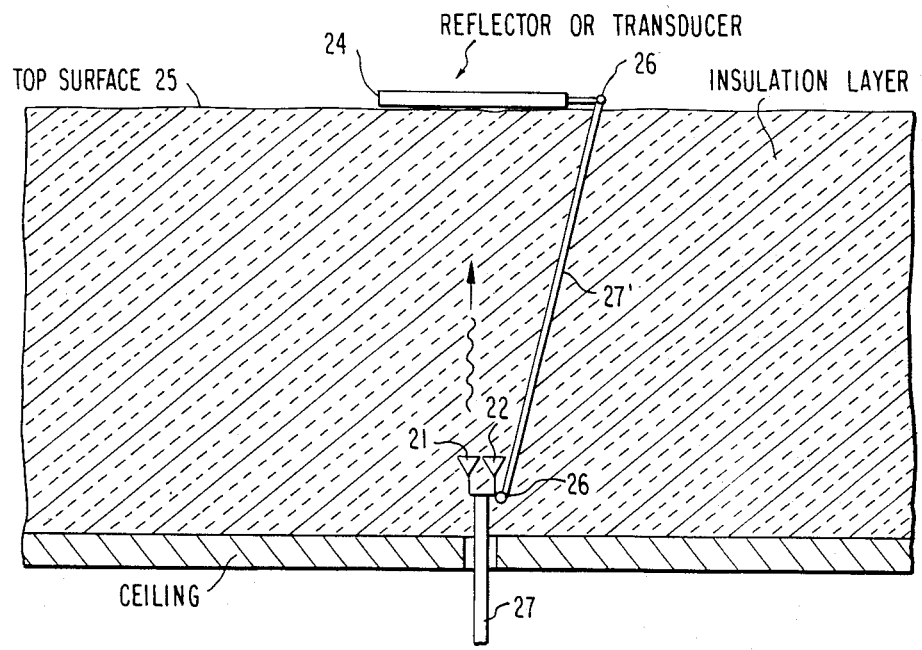
FIG. 6 is a third embodiment of the present invention wherein the two transducers are mounted on the end of a probe in a vertically spaced relation to a reflector (or transducer) also carried on the end of the probe.

In the embodiment of FIG. 6 the transmitting and receiving transducers 21 and 22, which may be one and the same transduction device, may be mounted in close proximity to each other on the end of a probe 27. A probe extension 27' is connected to the end of the probe 27 at one end thereof and to a reflecting target 24 at the opposite end thereof by means of articulation joints 26. The probe extension 27' may be retracted within the probe 27 during insertion through the ceiling hole and the target 24 may be collapsed in any suitable manner during insertion and subsequently extended to define a reflecting target in vertical alignment with the transducers 21 and 22. With the under surface of the target 24 resting on the upper surface 25 of the insulation layer an acoustic signal is transmitted from the transducer 21, reflected from the target 24 and received by the transducer 22. The target 24 may act as a reflector or as a transducer in which case the receiving transducer 22 on the end of the probe 27 would be unnecessary. The reflector or transducer 24 may be flat or curved to enhance the reflection or capture of the ultrasonic wave energy. The thickness and insulating value of the insulation layer can be calculated from the measurements made of the received acoustic signal.

Figure 7:
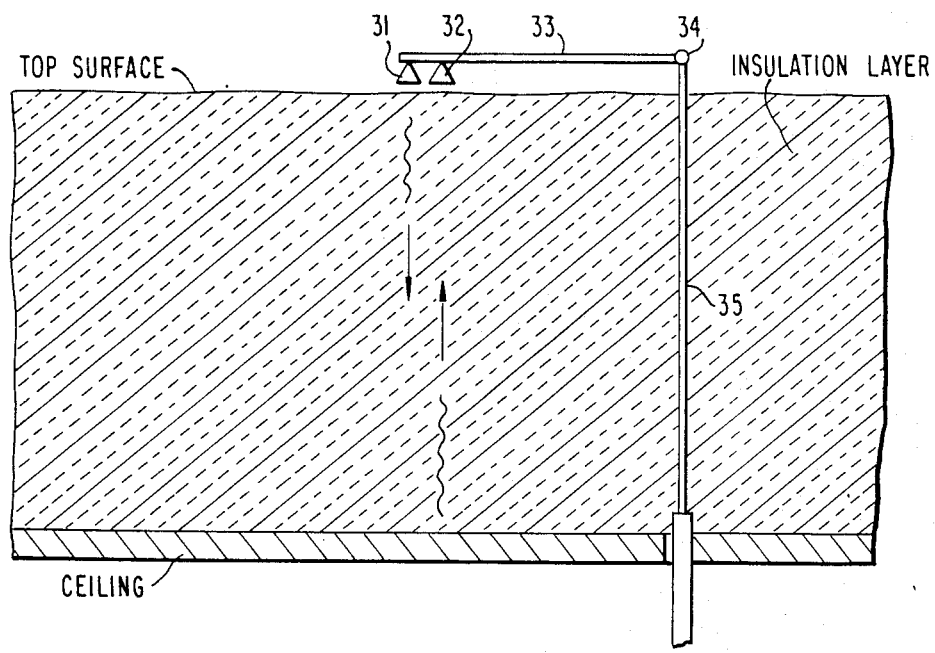
FIG. 7 shows a fourth embodiment according to the present invention wherein sending and receiving transducers are mounted on the end of a probe above the insulation whereby a signal from the sending transducer will be reflected off the ceiling back to the receiving transducer.

In the embodiment shown in FIG. 7 the transmitting transducer 31 and receiving transducer 32, which may be one and the same transducer are both mounted on the end of the probe extension 33 which is articulated at 34 to a probe 35 which extends through a small hole in the ceiling. The probe extension 33 may be collapsed against the probe 35 during insertion thereof through the insulation layer and subsequently unfolded to the position shown in FIG. 7. The acoustic signal transmitted by the transducer 31 will be reflected off the ceiling and received by the transducer 32 in order to determine the thickness and thermal value of the insulating layer.

In the embodiment of FIG. 8 the transmitting transducer 41 is adjacent the ceiling underside while the receiving transducer 42 is mounted on the probe extension 43 which is articulated at 44 to a probe 45 which extends through a small hole in the ceiling. The acoustic signal is transmitted through the ceiling and the insulation to be received by the transducer 42 in order to determine the thickness and thermal value of the insulating layer. Alternatively, a reflector inserted through a hole in the ceiling, or otherwise put in place, may be used in the position of the receiving transducer 42, in which case the receiving transducer would be located near the transmitting transducer as shown in FIG. 9.

While the invention has been particularly shown and described with reference to preferred embodiments thereof it will be understood by those in the art that the foregoing and other changes in form and details may be made therein without departing from the spirit and scope of the invention. For example, in those cases where access to the attic may be had by any means such as a scuttle hole, the invented technique may be applied without recourse to insertion of the apparatus through ceiling holes.

What is claimed is:

1. A method for measuring the density, thickness, and thermal conductivity of an insulation layer in an attic space above a ceiling comprising inserting at least one probe through a small aperture in the ceiling having transducer means thereon for transmitting and receiving acoustical signals, transmitting an acoustic signal from a first transducer through the insulation material to a second transducer and calculating the density, thickness, and thermal conductivity of the insulation by comparing the measurement of the received signal with standard values for the same type of insulation.

2. A method as set forth in claim 1 wherein two separate probes are inserted through two separate holes in the ceiling with the first transducer on one probe and the second transducer on another probe spaced a known distance from each other.

3. A method as set forth in claim 1 wherein both transducers are mounted adjacent each other on said probe and locating said transducers adjacent one surface of the insulation layer and locating a target adjacent the other surface of the insulation layer in vertical alignment with the transducers whereby a signal transmitted by said first transducer is reflected off the target and received by said second transducer.

4. An apparatus for the in situ acoustical measurement of insulation density and thickness comprising probe means adapted to be inserted through a small hole in a ceiling into contact with a layer of insulation material disposed on said ceiling, transducer means mounted on said probe means comprised of a first transducer and a second transducer adapted to transmit and receive an acoustic signal respectively with at least one of said first and second transducers being mounted on articulated extension means adjustably connected to said probe means, signal generator means connected to said first transducer for transmitting a signal from said first transducer and signal processing means connected to said second transducer for processing the received signal to determine characteristics of the insulation.

5. An apparatus as set forth in claim 4 wherein both of said transducers are mounted adjacent each other on said articulation means for being positioned adjacent the upper surface of the insulating material and oriented in the same direction whereby a signal transmitted from the first transducer will be reflected from the ceiling and received by the second transducer.

6. An apparatus for the in situ acoustical measurement of insulation material, density and thickness comprising a transducer means adapted to be mounted adjacent a ceiling underside, probe means adapted to be inserted through a small hole in a ceiling and having articulated means adjustably connected to said probe means and impingement means mounted on said articulated means means adjacent the upper surface of the insulating material whereby a signal transmitted from said transducer means impinges on said impingement means.

7. An apparatus as set forth in claim 6 wherein said transducer means is a combination receiver and sender and said impingement means is a reflector.

8. An apparatus as set forth in claim 6 wherein said transducer means is comprised of a first transducer adapted to send a signal and said impingement means is comprised of a second transducer adapted to receive a signal.

* * * * *